US006441213B1

(12) United States Patent
Musa et al.

(10) Patent No.: US 6,441,213 B1
(45) Date of Patent: Aug. 27, 2002

(54) ADHESION PROMOTERS CONTAINING SILANE, CARBAMATE OR UREA, AND DONOR OR ACCEPTOR FUNCTIONALITY

(75) Inventors: Osama M. Musa, Hillsborough, NJ (US); Colin McLean, Sawston (GB); Mark Bonneau, Brea, CA (US); Nikola A. Nikolic, Princeton, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/573,804

(22) Filed: May 18, 2000

(51) Int. Cl.[7] .................................................. C07F 7/04
(52) U.S. Cl. ........................ 556/418; 556/419; 556/420
(58) Field of Search ................................ 556/418, 419, 556/420

(56) References Cited

U.S. PATENT DOCUMENTS

| | | | |
|---|---|---|---|
| 4,486,582 A | 12/1984 | Heffner, Jr. .................. 526/301 |
| 4,543,397 A | 9/1985 | Woods et al. ................ 525/455 |
| 4,640,849 A | 2/1987 | Woods et al. ............... 427/54.1 |
| 4,732,956 A | 3/1988 | Woods et al. ................ 526/260 |
| 4,749,807 A | 6/1988 | Lapin et al. ................... 560/91 |
| 4,751,273 A | 6/1988 | Lapin et al. ................. 525/455 |
| 4,775,732 A | 10/1988 | Lapin et al. ................... 528/49 |
| 5,019,629 A | 5/1991 | Woods et al. ................ 525/312 |
| 5,084,490 A | 1/1992 | McArdle et al. ............. 522/181 |
| 5,183,946 A | 2/1993 | Liu et al. ..................... 568/670 |
| 5,334,456 A | 8/1994 | Noren et al. ................. 428/431 |
| 5,384,342 A | * 1/1995 | Szum .......................... 428/378 |
| 5,491,178 A | 2/1996 | Swedo et al. .................. 522/74 |
| 5,514,727 A | 5/1996 | Green et al. ................... 522/15 |
| 5,516,455 A | 5/1996 | Jacobine et al. ........ 252/299.01 |
| 5,539,014 A | 7/1996 | Swedo et al. .................. 522/91 |
| 5,633,411 A | 5/1997 | Woods et al. ................ 568/654 |
| 5,708,129 A | 1/1998 | Nguyen et al. .............. 528/362 |
| 5,789,757 A | 8/1998 | Husson, Jr. et al. .... 252/183.11 |
| 6,034,194 A | 3/2000 | Dershem et al. ............. 526/262 |
| 6,034,195 A | 3/2000 | Dershem et al. ............. 526/262 |

OTHER PUBLICATIONS

"Co–Polymerization of Maleimides and Vinyl Ethers: A Structural Study" by P. Kohli, A. B. Scranton, and G. J. Blanchard; *Macromolecules 1998, 31, 5681–5689.*

\* cited by examiner

*Primary Examiner*—Bernard Lipman
(74) *Attorney, Agent, or Firm*—Jane E. Gennaro

(57) ABSTRACT

An adhesion promoter containing silane, and carbamate, thiocarbamate or urea functionality, and electron donor or electron acceptor functionality, displays low volatility.

4 Claims, No Drawings

ADHESION PROMOTERS CONTAINING SILANE, CARBAMATE OR UREA, AND DONOR OR ACCEPTOR FUNCTIONALITY

FIELD OF THE INVENTION

This invention relates to adhesion promoters containing silane and polar functionality, such as carbamate, thiocarbamate, and urea, and electron donor or acceptor functionality, and particularly to adhesion promoters for use in coatings and on substrates for electronic applications.

BACKGROUND OF THE INVENTION

Adhesive compositions are used for a variety of purposes in the fabrication and assembly of semiconductor packages and microelectronic devices. The more prominent uses are the bonding of integrated circuit chips to lead frames or other substrates, and the bonding of circuit packages or assemblies to printed wire boards. Currently, lead frames are made of 42Fe/58Ni alloy (Alloy 42), copper, or silver- or palladium-coated copper, and wire boards of ceramic or laminate. Adhesives that have good performance for semiconductor packaging may, however, be deficient in adhesion to one or more of these substrates.

The addition of adhesion promoters would serve to correct this deficiency, but the commercially available adhesion promoters do not augment adhesion to all the substrates and the materials tend to volatilize significantly before the cure temperature of the adhesive is reached. Thus, there is a need for new adhesion promoters with enhanced reactivity and lower volatility than those currently commercially available.

SUMMARY OF THE INVENTION

This invention relates to adhesive or coating compositions containing adhesion promoters, and to the specific adhesion promoter compounds. The adhesion promoter compounds contain a silane functionality; a polar functionality, generally carbamate, urea, or thiocarbamate, to increase the adhesion normally promoted by the siloxane functionality; and an electron acceptor or electron donor moiety to react with other resins present in the adhesive composition.

The molecular weight of these compounds may readily be adjusted for a particular curing profile so that the compound does not volatilize during curing.

DETAILED DESCRIPTION OF THE INVENTION

The adhesion promoters of this invention have the structure

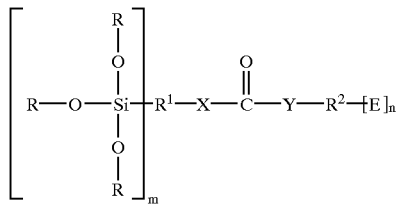

in which m and n independently are 1 to 6, preferably 1 to 3, and more preferably 1;

R is a $C_1$ to $C_6$ alkyl group, or an aromatic or heteroaromatic ring or fused ring having 3 to 10 carbon atoms within the ring structure, in which the heteroatoms may be N, O, or S;

$R^1$ and $R^2$ independently are a linear or branched chain alkyl or alkyloxy group having 2 to 100 carbon atoms, which chain may have cyclic moieties, X and Y are O, S or $N(R^3)$ with the proviso that X and Y may not both be O or S, and in which $R^3$ is a $C_1$ to $C_4$ alkyl, preferably is hydrogen, methyl, or ethyl, and more preferably is hydrogen;

and E is an electron donating or electron accepting group.

Suitable electron acceptor groups are, for example, maleimides, acrylates, fumarates and maleates. Suitable electron donor groups are, for example, vinyl ethers, and carbon to carbon double bonds external to an aromatic ring and conjugated with the unsaturation in the aromatic ring.

The activity of the electron donor functionality other than the vinyl ether functionality can be increased by adding electron donating substituents on the aromatic ring, or decreased by adding electron withdrawing substituents. The activity can also be varied by steric interaction. An increase in the number or size of alkyl substituents on the carbon to carbon double bond conjugated with the aromatic ring or the carbon to carbon double bond of the vinyl ether group will decrease the reactivity. Preferably, any substituents on the carbon to carbon double bonds will be hydrogen, or will be hydrogen with methyl as only one of the substituents.

One method of preparation of the adhesion promoter compounds proceeds through a reaction between a first starting compound containing the electron donor or electron acceptor and the $R^2$ group and a second starting compound containing the silane and the $R^1$ group. The $R^1$ and $R^2$ groups will each contain a co-reactive functionality, such that the reactive functionality on the $R^1$ group will react with the functionality on the $R^2$ group. Examples of co-reactive functionalities are alcohol, thiol or amine, which would react with an isocyanate. The choice of reactants in practice will be determined by commercially available starting materials. In theory, the choice of reactants can be chosen by the practitioner to achieve the desired end compound, but in any case, the chemical linkage will be a carbamate, thiocarbamate, or urea linkage.

Examples of suitable starting materials containing the siloxane functionality are gamma-isocyanatopropyltriethoxysilane, gamma-aminopropyltriethoxysilane, gamma-aminopropyltrimethoxysilane, N-beta-(aminoethyl)-gamma-aminopropyltrimethoxysilane, triaminofunctional silane, bis-(gamma-trimethoxysilylpropyl)amine, N-phenyl-gamma-am inopropyl-trimethoxy-silane, N-beta-(aminoethyl )-gamma-aminopropylmethyldimethoxysilane, and gamma-mercaptopropyltrimethoxysilane.

Examples of suitable starting materials containing an electron donor functionality are hydroxybutyl vinyl ether, cinnamyl alcohol, 1,4-cyclohexane-dimethanol monovinyl ether, 3-isopropenyl-α,α-dimethylbenzyl isocyanate, N-(6-hydroxyhexyl) maleimide and isoeugenol.

Examples of suitable starting materials containing an electron acceptor functionality are dioctyl maleate, dibutyl maleate, dioctyl fumarate, dibutyl fumarate, and maleimides.

The adhesion promoters are formulated into adhesive, coating, potting or encapsulant compositions. The formulations typically will contain a curable resin one or more curing agents, and may contain a conductive or nonconductive filler, in addition to the adhesion promoter.

In general the silane adhesion promoters will be present in such compositions in an amount ranging from 0.005 to 15.0 weight percent of the composition.

Curable resins are many and varied and well-known to practitioners in the adhesive, coating, potting and encapsulant arts, and can be chosen by the practitioner to meet a specific end use.

Exemplary curing agents are thermal initiators and photoinitiators present in the adhesive composition in an amount of 0.1% to 10%, preferably 0.1% to 3.0%, by weight of the electron donor compound. Preferred thermal initiators include peroxides, such as butyl peroctoates and dicumyl peroxide, and azo compounds, such as 2,2'-azobis(2-methylpropanenitrile) and 2,2'-azobis(2-methyl-butanenitrile). A preferred series of photoinitiators is one sold under the trademark Irgacure by Ciba Specialty Chemicals. In some formulations, both thermal initiation and photoinitiation may be desirable, for example, the curing process can be started by irradiation, and in a later processing step curing can be completed by the application of heat to accomplish the thermal cure.

In general, these compositions will cure within a temperature range of 70° C. to 250° C., and curing will be effected within a range of ten seconds to three hours. The time and temperature curing profile of each formulation will vary with the specific electron donor compound and the other components of the formulation, but the parameters of a curing profile can be adjusted by a practitioner skilled in the art without undue experimentation.

Suitable conductive fillers are carbon black, graphite, gold, silver, copper, platinum, palladium, nickel, aluminum, silicon carbide, boron nitride, diamond, and alumina. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. When present, fillers will be in amounts of 20% to 90% by weight of the formulation.

The following examples are intended as an illustration of the invention and are not to be construed as a limitation.

EXAMPLE 1

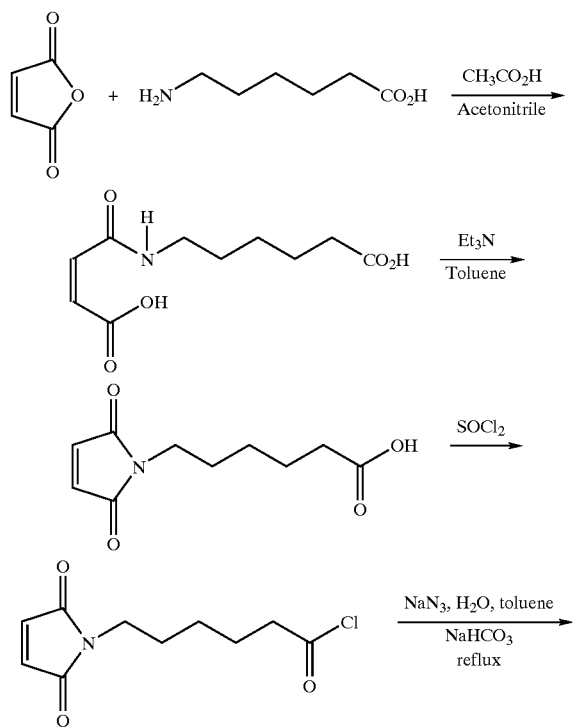

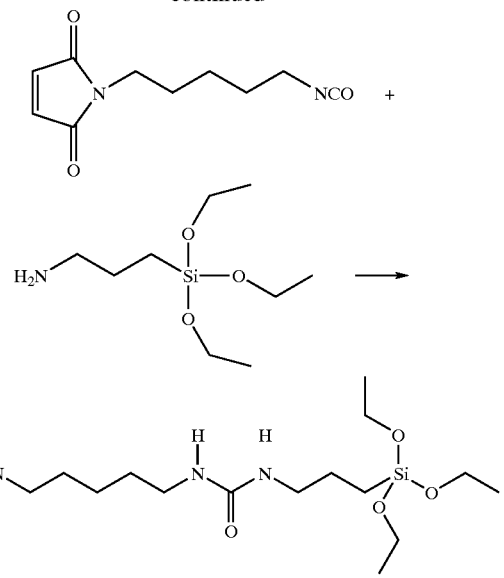

A solution of one mole equivalent maleic anhydride in acetonitrile is added to one equivalent 6-aminocaproic acid in acetic acid. The mixture is allowed to react for three hours at room temperature. The formed white crystals are filtered off, washed with cold acetonitrile and dried to yield the amic acid adduct.

The amic acid adduct is mixed with triethylamine in toluene. The mixture is heated to 130° C. for two hours and water is collected in a Dean-Stark trap. The organic solvent is evaporated and 2M HCl is added to reach pH 2. The product 6-maleimidocaproic acid is recovered by extraction with ethyl acetate, drying over $MgSO_4$, and evaporation of the solvent.

6-Maleimidocaproic acid is treated with excess thionyl chloride at 50° C. for three hours. Remaining thionyl chloride is distilled off to leave the product, 6-maleimidocaproic chloride.

With vigorous stirring, a mixture of one mole equivalent sodium azide in water, toluene and a catalytic amount of benzyltriethylammonium chloride is cooled to approximately 10° C. in around-bottom flask. One mole equivalent of 6-maleimidocaproic chloride is added dropwise to that solution over approximately 40 minutes. Stirring of the solution is continued for one hour at 15° C. and for one hour at 20° C. The organic phase is separated off in a separating funnel and washed with 2N aqueous sodium bicarbonate solution and with water. The organic phase is dried with $MgSO_4$ and filtered. The filtrate is introduced into a round-bottom flask and heated slowly to reflux temperature. Reflux is maintained until the evolution of nitrogen has ceased. The solution is heated under reflux for a further 30 minutes and, after cooling, is poured into a round-bottom flask. The solution is concentrated using a rotary evaporator and the residue is distilled under a high vacuum to produce the maleimide with isocyanate functionality.

One mole equivalent of maleimide with isocyanate functionality is solvated in toluene in a three-necked flask equipped with a mechanical stirrer, addition funnel and nitrogen inlet/outlet. The reaction is placed under nitrogen, and the solution is heated to 70° C. The addition funnel is charged with one mole equivalent gamma-aminopropyltriethoxysilane (Witco Corp., Silquest A-1100) dissolved in toluene. This solution is added to the isocyanate solution over ten minutes, and the resulting mixture heated for an additional three hours at 70° C. After the reaction is allowed to cool to room temperature, the mixture is washed with distilled water three times. The isolated organic layer is dried over MgSO$_4$, filtered and the solvent removed in vacuo to give the product.

EXAMPLE 2

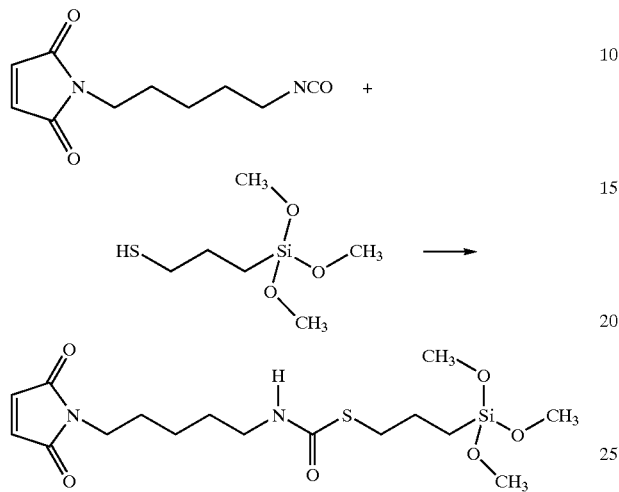

One mole equivalent of maleimide with isocyanate functionality from Example 6 is solvated in toluene in a three-necked flask equipped with a mechanical stirrer, addition funnel and nitrogen inlet/outlet. The reaction is placed under nitrogen, and the solution is heated to 70° C. The addition funnel is charged with one mole equivalent gamma-mercaptopropyl-trimethoxysilane (Witco Corp., Silquest A-189) dissolved in toluene. This solution is added to the isocyanate solution over ten minutes, and the resulting mixture heated for an additional three hours at 70° C. After the reaction is allowed to cool to room temperature, the mixture is washed with distilled water three times. The isolated organic layer is dried over MgSO$_4$, filtered, and the solvent removed in vacuo to give the product.

EXAMPLE 3

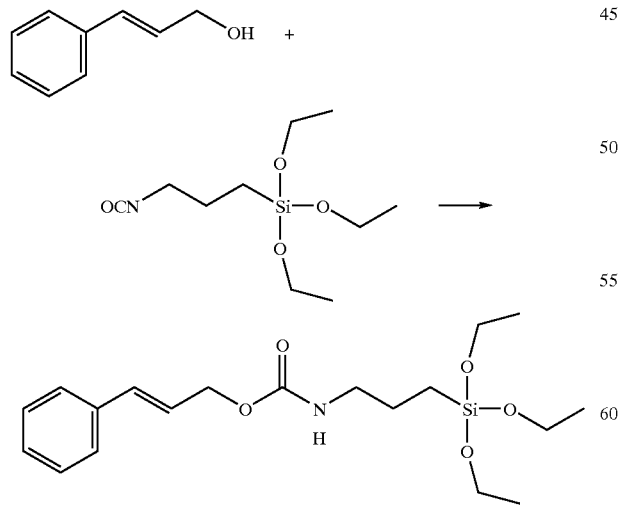

Gamma-isocyanatopropyltriethoxysilane (Witco Corp., Silquest A-1310) (34.1 g, 0.134 mole) was solvated in toluene (100 mL) in a 500 mL three-necked flask equipped with a mechanical stirrer, addition funnel and nitrogen inlet/outlet. The reaction was placed under nitrogen, and 0.02 g of dibutyltin dilaurate (catalyst) was added with stirring as the solution was heated to 80° C. The addition funnel was charged with cinnamyl alcohol (18.5 g, 0.134 mole) dissolved in toluene (50 mL). This solution was added to the isocyanate solution over ten minutes, and the resulting mixture was heated for an additional three hours at 80° C. After the reaction was allowed to cool to room temperature, the mixture was washed with distilled water three times.

The isolated organic layer was dried over MgSO$_4$, filtered and the solvent removed in vacuo to give the product in 95% yield.

EXAMPLE 4

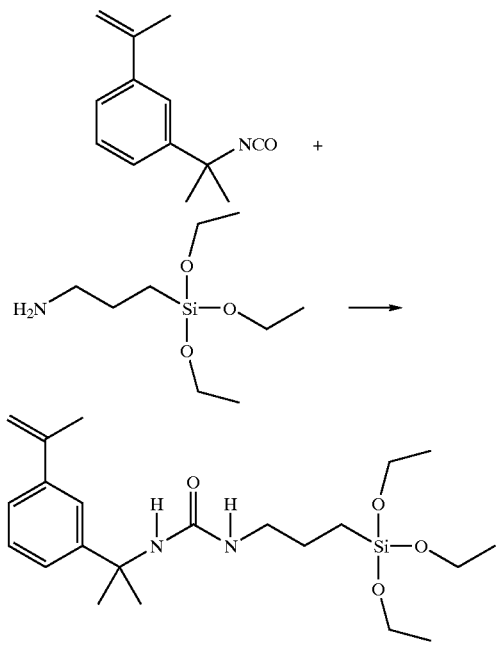

Gamma-aminopropyltriethoxysilane (Witco Corp., Silquest A-1100) (20 g, 0.09 mole) was solvated in toluene (100 mL) in a 500 mL three-necked flask equipped with a mechanical stirrer, addition funnel and nitrogen inlet/outlet. The reaction was placed under nitrogen, and the solution heated to 50° C. The addition funnel was charged with 3-isopropenyl-(α,α-dimethylbenzyl isocyanate (m-TMI) (18.2 g, 0.09 mole) dissolved in toluene (50 mL). This solution was added to the amine solution over ten minutes, and the resulting mixture was heated for an additional one hour at 50° C.

After the reaction was allowed to cool to room temperature, the mixture was washed with distilled water three times. The isolated organic layer was dried over MgSO$_4$, filtered and the solvent removed in vacuo to give the product in 96% yield.

EXAMPLE 5

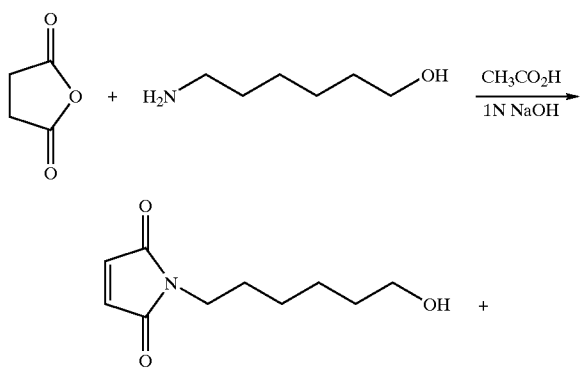

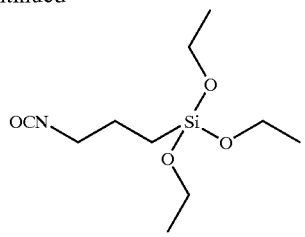

One mole equivalent of maleic anhydride and one mole equivalent of 6-amino hexanol are dissolved in anhydrous acetic acid and the solution is heated under reflux for eight hours. The acetic acid is distilled off in a rotary evaporator. The residue is dissolved in diethyl ether and washed once with 1 N NaOH, and twice with water. After drying over MgSO4 and evaporating the diethyl ether, the residue is crystallized from isopropyl ether to produce N-(6-hydroxyhexyl) maleimide.

One mole equivalent of gamma-isocyanatopropyltriethoxysilane (Witco Corp., Silquest A-1310) is solvated in toluene in a three-necked flask equipped with a mechanical stirrer, addition funnel and nitrogen inlet/outlet. The reaction is placed under nitrogen, and 0.01 mole equivalent dibutyltin dilaurate (catalyst) is added with stirring as the solution is heated to 90° C. The addition funnel is charged with one mole equivalent N-(6-hydroxyhexyl) maleimide dissolved in toluene. This solution is added to the isocyanate solution over ten minutes, and the resulting mixture heated for an additional three hours at 90° C. After the reaction is allowed to cool to room temperature, the mixture is washed with distilled water three times. The isolated organic layer is dried over MgSO$_4$, filtered and the solvent removed in vacuo to give the product.

EXAMPLE 6

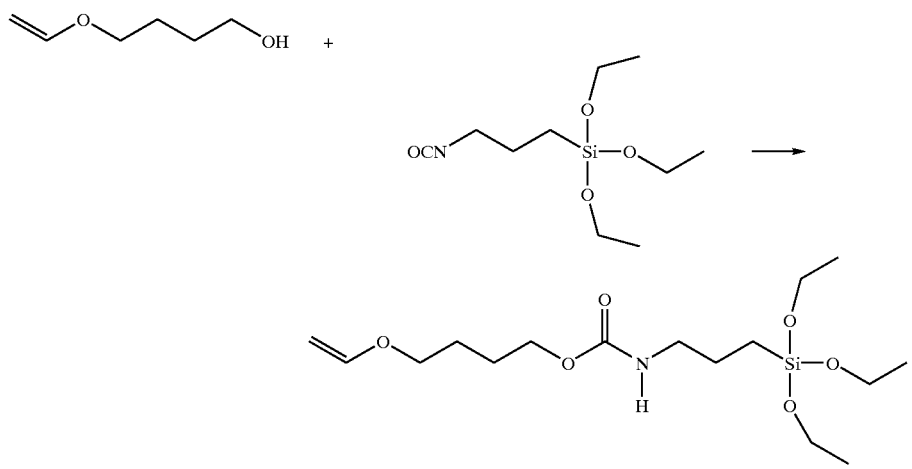

Gamma-isocyanatopropyltriethoxysilane (Witco Corp., Silquest A-1310) (42.6 g. 0.172 mole) was solvated in toluene (100 mL) in a 500 mL three-necked flask equipped with a mechanical stirrer, addition funnel and nitrogen inlet/outlet. The reaction was placed under nitrogen, and 0.02 g of dibutyltin dilaurate (catalyst) was added with stirring as the solution was heated to 50° C. The addition funnel was charged with hydroxybutyl vinyl ether (BASF) (20 g, 0.172 mole) dissolved in toluene (50 mL). This solution was added to the isocyanate solution over ten minutes, and the resulting mixture heated for an additional four hours at 50° C. After the reaction was allowed to cool to room temperature, the mixture was washed with distilled water three times. The isolated organic layer was dried over MgSO$_4$, filtered and the solvent removed in vacuo to give the product in 95% yield.

EXAMPLE 7

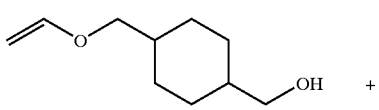

9
-continued

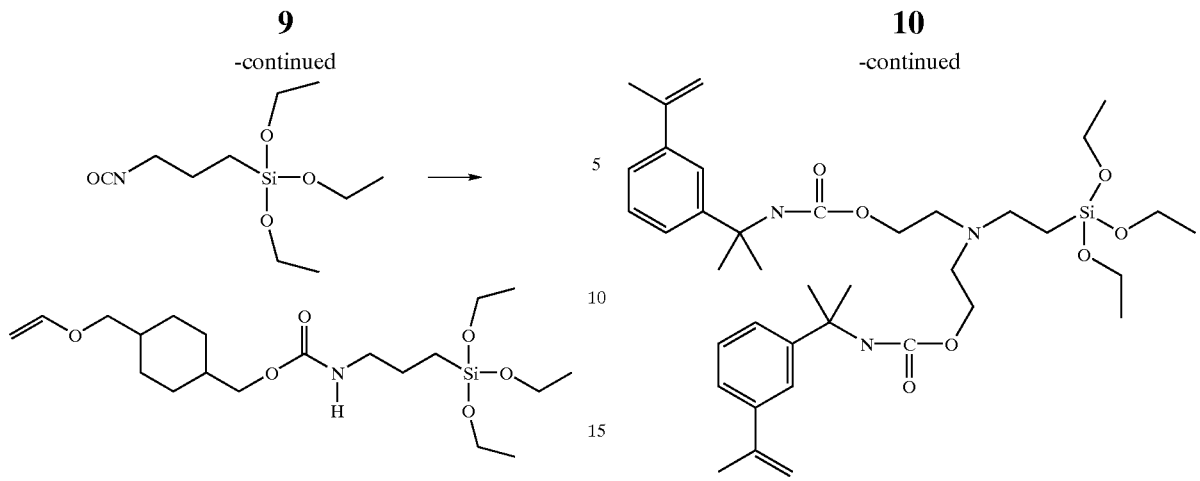

Gamma-isocyanatopropyltriethoxysilane (Witco Corp., Silquest A-1310) (29.02 g, 0.118 mole) was solvated in toluene (100 mL) in a 500 mL three-necked flask equipped with a mechanical stirrer, addition funnel and nitrogen inlet/outlet. The reaction was placed under nitrogen, and 0.02 g of dibutyltin dilaurate (catalyst) was added with stirring as the solution was heated to 50° C. The addition funnel was charged with 1,4-cyclohexanedimethanol monovinyl ether (BASF) (20 g, 0.118 mole) dissolved in toluene (50 mL). This solution was added to the isocyanate solution over ten minutes, and the resulting mixture was heated for an additional three hours at 80° C. After the reaction was allowed to cool to room temperature, the mixture was washed with distilled water three times. The isolated organic layer was dried over MgSO$_4$, filtered and the solvent removed in vacuo to give the product in 94% yield.

EXAMPLE 8

This example shows a reaction scheme for obtaining a compound with two electron donor groups.

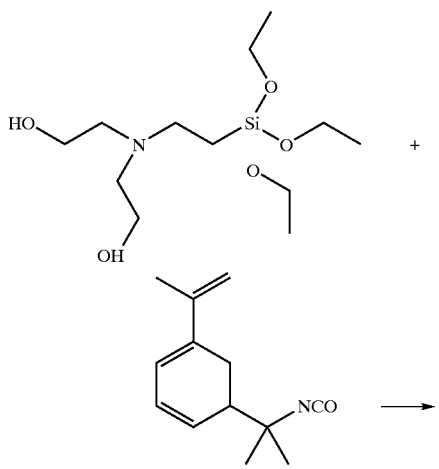

10
-continued

EXAMPLE 9

The viscosity and percent weight loss of adhesion promoters from the previous examples were compared to the viscosity and percent weight loss of an adhesion promoter commercially available from Witco Corp as Silquest A-174 having ester functionality, and no carbamate or urea functionality. The Silquest A-1 74 adhesion promoter has the following structure:

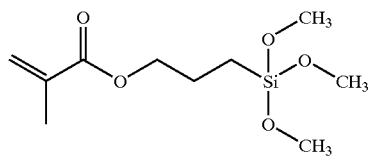

The viscosity was determined on a Brookfield viscometer, spindle #51, 10 rpm, and the percent weight loss determined by TGA (thermogravimetric analysis) with a rpm rate of 10° C./minute with measurement at 200° C. The results for the neat compounds are shown in the following table.

| Adhesion promoter | Viscosity (cPs) at 25° C. | Weight Loss at 200° C. |
|---|---|---|
| Silquest A-174 | 5 | 99.6% |
| example 1 | 30 | 23.0% |
| example 2 | 120 | 9.7% |
| example 3 | 70 | 8.1% |

The data show that the viscosity is lower and the volatility is higher for the commercially available material compared to the example adhesion promoters.

These adhesion promoters next were formulated into adhesive formulations containing the following components:

| | |
|---|---|
| 5.0 g | ester-linked bismaleimide |
| 5.0 g | carbamate-linked bis styrene |
| 1.15 g | (poly)butadiene rubber grafted with 8% maleic anhydride |
| 0.115 g | adhesion promoter |
| 0.23 g | initiator (Witco, USP-90MD) |
| 34.5 g | silver flake |

The ester-linked bismaleimide had the following structure:

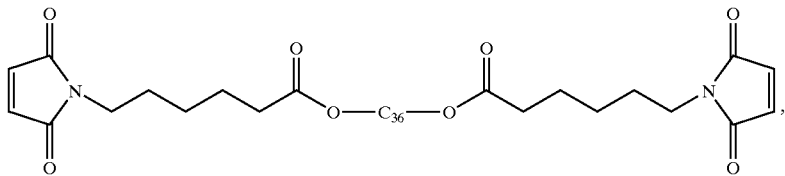

in which $C_{36}$ represents a mixture of isomers of a linear or branched alkyl chain having 36 carbon atoms, resulting from the dimerization of linoleic acid and oleic acid. The dimer acid is converted to the alcohol and then reacted with 6-maleimido-caproic acid to form the bismaleimide.

The carbamate-linked styrenic had the following structure:

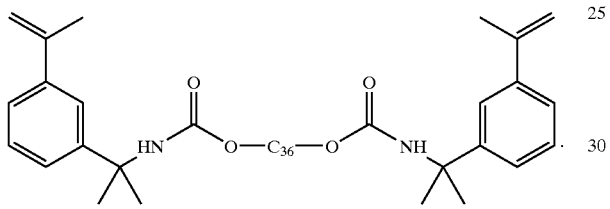

in which $C_{36}$ represents a mixture of isomers of a linear or branched alkyl chain having 36 carbon atoms, resulting from the dimerization of linoleic and oleic acids. The dimer acid is converted to the alcohol and then reacted with the 3-isopropenyl-α,α-dimethylbenzyl isocyanate to form the carbamate linked styrenic compound.

The formulations were tested for volatility during the curing process and for identification of the adhesion promoter by headspace GC. Total weight loss of the adhesive formulation was tested by TGA. The results are set out in the following table and show that the formulations containing the adhesion promoters described in this specification have a lower weight loss than those prepared with the commercial adhesion promoter.

| Base Formulation and identified adhesion promoter | Head Space GC Amount Released | TGA Weight Loss at 200° C. |
|---|---|---|
| Silquest A-174 | 640 ppm | 0.53% |
| example 1 | 610 ppm | 0.51% |
| example 2 | 45 ppm | 0.32% |
| example 3 | 36 ppm | 0.29% |

We claim:

1. An adhesion promoter having the structure

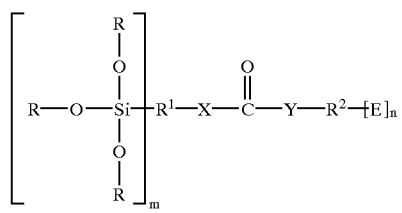

in which m and n independently are 1 to 6;

R is a $C_1$ to $C_3$ alkyl group or an aromatic or heteroaromatic ring or fused ring having 3 to 10 carbon atoms within the ring structure, in which the heteroatoms may be N, O, or S;, $R^1$ and $R^2$ independently are a linear or branched chain alkyl or alkyloxy group that have 2 to 100 carbon atoms, which chain may have cyclic moieties, E is a maleimide group or a group containing carbon to carbon double bonds connected to an aromatic ring and conjugated with the unsaturation in the ring, and X and Y are O, S or $N(R^3)$ with the proviso that X and Y may not both be O or S, and in which $R^3$ is a $C_1$ to $C_4$ lower alkyl.

2. The adhesion promoter according to claim 1 having the structure:

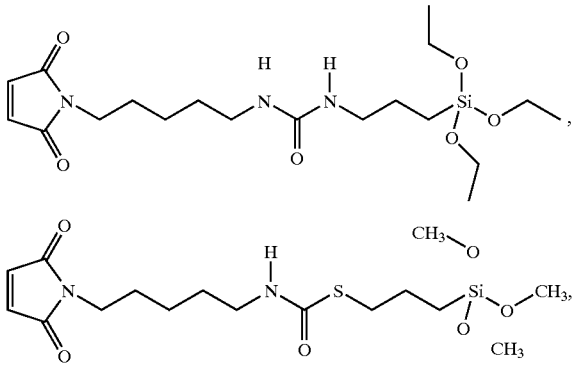

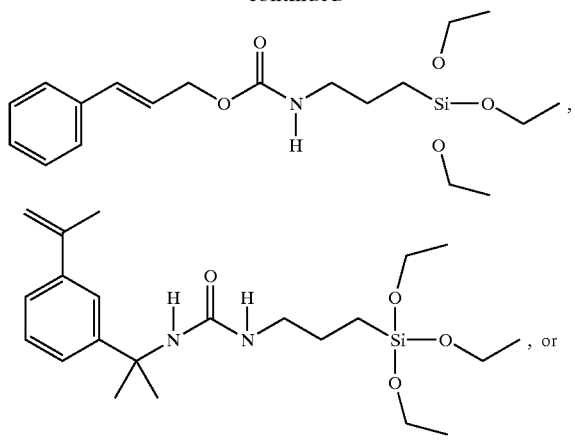
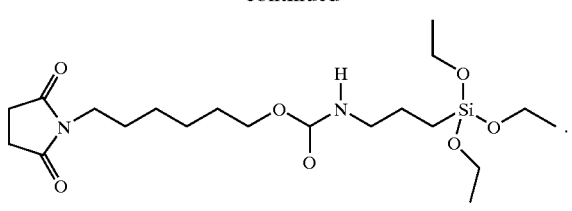
3. An adhesive composition comprising a curable resin, a curing agent, and an adhesion promoter according to claim 1.
4. The adhesive composition according to claim 3 further comprising a conductive or non-conductive filler.
* * * * *